(12) United States Patent
Stiller

(10) Patent No.: US 11,240,987 B2
(45) Date of Patent: Feb. 8, 2022

(54) COTTON VARIETY SICOT 714B3F

(71) Applicants: Commonwealth Scientific and Industrial Research Organisation, Acton ACT (AU); Cotton Seed Distributors Ltd, Wee Waa (AU)

(72) Inventor: Warwick Nigel Stiller, Acton ACT (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 0 days.

(21) Appl. No.: 15/693,519

(22) Filed: Sep. 1, 2017

(65) Prior Publication Data

US 2018/0054994 A1 Mar. 1, 2018

(30) Foreign Application Priority Data

Sep. 1, 2016 (AU) ................................ 2016222448

(51) Int. Cl.
*A01H 6/60* (2018.01)
*A01H 5/10* (2018.01)
*C12N 5/04* (2006.01)

(52) U.S. Cl.
CPC ............... *A01H 6/604* (2018.05); *A01H 5/10* (2013.01); *C12N 5/04* (2013.01)

(58) Field of Classification Search
CPC ....................................................... A01H 5/10
See application file for complete search history.

(56) References Cited

U.S. PATENT DOCUMENTS

2015/0150208 A1* 6/2015 McPherson ............... A01H 5/10
800/260

OTHER PUBLICATIONS

Plant Varieties Journal, vol. 21, No. 3, Dec. 2008.*
Dow AgroSciences Australia, Risk assessment and risk management plan, DIR 040/2003, Nov. 2003.*
Cotton Seed Distributors, New Variety—Sicot 71BRF, Jul. 2009.*

* cited by examiner

*Primary Examiner* — Mykola V. Kovalenko
(74) *Attorney, Agent, or Firm* — Buchanan Ingersoll & Rooney PC

(57) ABSTRACT

The present invention provides a plant of the cotton (*Gossypium hirsutum*) variety Sicot 714B3F, or a part, cell, tissue or organ thereof.

19 Claims, No Drawings

COTTON VARIETY SICOT 714B3F

FIELD OF THE INVENTION

The present invention relates to a new cotton (*Gossypium hirsutum*) variety, and more particularly to cotton plants and cotton seeds of this new variety. The invention also relates to F1 hybrid cotton plants and seeds produced using the new variety, as well as to cotton plants and seeds produced by transformation of this new variety and progeny thereof.

BACKGROUND OF THE INVENTION

Cotton is an important and valuable field crop which is used to manufacture textile products, oil, animal feed, cordage and other non-woven products. Cotton production today is based mainly on cultivation of varieties of the species *Gossypium hirsutum*, known as Upland cotton. These cotton varieties are generally preferred for their high lint yield potential, early maturity, and adaptation to adverse climatic and growing conditions. On the other hand, the quality of Upland cotton lint is considered low to medium.

Varieties of another species, *G. barbadense*, known as Pima cotton, constitute only 5-8% of the world cultivated cotton area. Pima varieties typically produce superior lint having long, strong and fine fibre. On the other hand, these varieties usually have low yield potential, require a long growing season, and can only be cultivated in warm regions. Cotton lint quality is measured by a number of measures including fibre length, strength and micronaire. Accordingly, the lint quality is considered higher when the fibre is longer, stronger and finer when the fibre is fully matured in open bolls.

One of the main constraints on cotton production worldwide is the damage caused by insect pests such as the cotton bollworm (*Helicoverpa* sp.). In the last 20 years, cotton has been genetically engineered by the insertion of transgenes encoding insecticidal proteins from *Bacillus thuringiensis* (Bt), thereby providing in planta production of the Bt proteins in leaves and bolls and a degree of protection against the insect pests. This has resulted in a substantial decrease in the use of chemical insecticides by spraying, with environmental benefits. However, the emergence of insect pests which are tolerant to the Bt proteins remains a concern and integrated pest management strategies including the use of, for example, non-transgenic refugia are important. More recently, the adoption of cotton cultivars expressing two Bt proteins with different modes of action has been an important development. For example, the Bollgard II varieties incorporate transgenes for expression of Cry1Ac and Cry2Ab proteins and have been grown in various countries including Australia for 10 years. However, the potential emergence of pest populations having resistance to the Bt proteins remains a concern (Downes et al, J. Invertebrate Pathol. 110:281-286, 2012).

An alternative, non-Bt insecticidal protein, Vip3A, has been proposed to be combined with the dual Bt proteins. Cotton plants expressing Vip3A have been produced. However, expression levels of the Vip3A protein declined as the season progressed, leading to concerns about its effectiveness (Llewellyn et al, Agric. Forest Entomol. 9:93-101, 2007).

Transgenic cotton cultivars engineered for insect pest tolerance also need to be agronomically suitable and capable of producing lint at high yield and quality, to be commercially acceptable. This is a great challenge to cotton plant breeders when introducing the transgenes into locally adapted varieties. Due to the environment, the complexity of the structure of genes and location of a gene in the genome, among other factors, it is difficult to predict the phenotypic expression of a particular genotype in different genetic backgrounds. In addition, plant breeding applies to the phenotype and not on the level of the genotype. Therefore, a newly bred variety is considered to be an unexpected result of the breeding process. In particular, each variety will typically contain a unique combination of known and novel characteristics, based not just on the introduced transgenes but also to the totality of the genetic background.

There remains a need for well adapted cotton varieties with in planta insect tolerance and which produce lint at high yield and quality.

SUMMARY OF THE INVENTION

The present invention relates to seeds, plants, plant cells, parts of plants, cotton lint or fiber, and cotton textiles of the cotton variety designated as Sicot 714B3F, as well as to hybrid cotton plants and seeds obtained by repeatedly crossing plants of Sicot 714B3F with other cotton plants. The invention encompasses plants and plant varieties produced by the method of essential derivation from plants of Sicot 714B3F and to plants of Sicot 714B3F reproduced by vegetative methods, including but not limited to, regeneration of embryogenic cells or tissue of Sicot 714B3F.

According to one aspect of this invention, there is provided a plant of the cotton (*Gossypium hirsutum*) variety Sicot 714B3F, or a part, cell, tissue or organ thereof. Embodiments of this aspect of the present invention preferably relate to seed of the cotton plant; a tissue culture of regenerable cells of the cotton plant; a tissue culture regenerating plants, preferably capable of expressing all the morphological and physiological characteristics of the cotton plant; and a tissue culture regenerated from cells or protoplasts of a tissue selected from the group consisting of seeds, leaves, stems, pollens, anthers, ovules, embryos, and preferably cotyledons and hypocotyls.

The present invention also relates to a cotton plant produced by growing the seed as described above, or regenerated from a tissue culture as described above, or a part, cell, tissue or organ of such a plant.

According to another aspect of the present invention there is provided a method for producing an F1 hybrid cotton plant using plant breeding techniques which employ the cotton plant as described above, or a part, cell, tissue or organ thereof, as a source of plant breeding material. That is, a Sicot 714B3F plant is used as one parent, either male or female, in a cross to produce the F1 hybrid cotton plant. The method of this aspect of the invention further relates to plant breeding techniques selected from the group consisting of recurrent selection, backcrossing, pedigree breeding, marker assisted selection, genetic marker enhanced selection, and transformation. The invention therefore also provides progeny plants and plant parts such as seeds which are produced from an F1 hybrid cotton plant resulting from the method of this aspect.

In yet another aspect, the invention provides a method for producing a cotton plant comprising a further transgene by transformation of a cotton plant as described above, or a part, cell, tissue or organ thereof.

DETAILED DESCRIPTION OF THE INVENTION

As use herein, a "Cry protein" refers to a crystal protein from *B. thuringiensis* (Bt) which has insecticidal activity.

These include the Cry1Ac protein from *B. thuringiensis* var. *kurstaki* (Berliner) and the Cry2Ab protein. The levels of these proteins expressed in transgenic plants can be measured by ELISA assays as described in Example 1 herein.

As used herein, a "Vip protein" is a vegetative insecticidal protein from Bt. Vip proteins are produced during vegetative growth of Bt rather than just at sporulation as occurs for Cry proteins (reviewed by Chakroun et al, Microbiol. Mol. Biol. Reviews 80:329-350, 2016). Vip proteins must be activated by gut proteases in the insects after ingestion and bind to specific, but different, receptors in the insect midgut. Cotton lines expressing the Vip3A protein have been developed by Syngenta (Research Triangle Park, North Carolina) (Llewellyn et al., 2007, ibid).

As used herein, the terms "lint yield" or "yield" refer to the measure of the quantity of fibre produced, after ginning, on a given unit of land, for example bales/hectare (b/ha) or preferably kilograms/hectare (kg/ha).

As used herein, lint % (also known as "gin turnout") refers to the weight of the lint after ginning as a percentage of the weight of the seed cotton.

As used herein, the terms "fibre length" or "length" refer to the 2.5% span length in inches (or 32nds=1/32 inch) of fibre as measured by High Volume Instrumentation (HVI). Such instrumentation and methods for use are standard and well known in the industry.

As used herein, the terms "fibre strength" or "strength" refer to the force required to break a bundle of fibres as measured in grams/tex on the HVI.

As used herein, the term "micronaire" refer to the fibre periphery at maturity as measured in micronaire values ranging from about 2.0 (very fine) to 6.0 (very course). Micronaire values of about 3.8 to 4.6 are mid-range or average fineness.

As used herein, short fibre index is related to the uniformity of fibre length, as measured on the HVI. Values below 4.8 or even 4.5 are preferred.

As used herein, fibre elongation is a measure of how much the fibre stretches before it breaks, as measured on the HVI.

As used herein, the "adult %" in the context of wilt disease resistance is the percentage of uninfected seedlings which remain uninfected by *Fusarium* when grown to full size. The "total %" refers to the percentage of full size plants which remain uninfected. The *Fusarium* resistance ranking (F.rank) for a particular line is calculated as the total % for a particular line divided by the total % for the reference variety Sicot 189, expressed as a percentage. Sicot 189 is a relatively resistant variety to *Fusarium* and therefore a *Fusarium* resistance ranking of at least 100 was preferred.

As used herein, the term "parts" includes, but is not limited to, pollen, ovule, flowers, bolls, lint, linters, shoots, roots, leaves and preferably seeds of a plant.

Cotton is an important and valuable field crop. Thus, a primary goal of cotton breeding is to select and develop plants that have the traits that result in superior varieties. Parent plants, which have been selected for good agronomic and fiber quality traits are manually crossed in different combinations. The resulting F1 (Filial generation 1) plants are self-fertilized and the resulting F2 generation plants, which show a large variability on account of gene segregation, are planted in a selection field. These F2 plants are observed during the growing season for health, growth vigor, plant type, plant structure, leaf type, stand ability, flowering, maturity, seed yield, boll type, boll distribution, boll size, fiber yield and fiber quality. Plants are then selected. The selected plants are harvested, the bolls are analyzed for fiber characteristics and the seeds are cleaned and stored. This procedure is repeated in the following growing seasons, whereby the selection and testing units increase from individual plants in the F2, to multiple plants containing 'lines' (descending from one mother plant) in the F5 and the number of units decrease from approximately 500 plants in the F2 to 20 lines in the F5 by selecting about 10-20% of the units in each selection cycle. The increased size of the units, whereby more seed per unit is available, allows the selection and testing in replicated trials on more than one location with a different environment and a more extensive and accurate analyzing of the fiber quality. The lines or candidate varieties become genotypically more homozygous and phenotypically more homogeneous by selecting similar plant types within a line and by discarding the so called off-types from the very variable F2 generation on to the final F7 or F8 generation. Depending on the intermediate results the plant breeder may decide to vary the procedure as described above such as by accelerating the process by testing a particular line earlier or retesting a line another year. He may also select plants for further crossing with existing parent plants or with other plants resulting from the current selection procedure.

Plants. The inventor has carried out such a breeding program using as parental lines a variety Sicot 71BRF and a proprietary breeding line designated 69801F1, the latter not available to the public. Parental variety Sicot 71BRF was commercially released in 2010-11 and was transgenic for genes expressing Cry1Ac and Cry2Ab insecticidal proteins and a T-DNA having two CP4 genes within the T-DNA which together provide tolerance to the herbicide glyphosate. The CP4 genes provide tolerance to the cotton plant throughout the growing season, allowing application of the herbicide and therefore weed control in the fields throughout the season. Such a genetic variation is known as "Roundup Ready Flex" gene. Sicot 71BRF has good pest and disease resistance and provides quality fibre of moderate length (typically about 1.22") and good strength (31.9), micronaire of 4.2. Breeding line 69801F1 comprises a gene encoding the insecticidal Vip3A gene. The present inventor was able to not only combine the four transgenes, three from Sicot 71BRF and one from 69801F1, but was also able to produce a new variety with superior properties including unexpectedly high disease tolerance, particularly to *Verticillium* wilt, while maintaining yield and fibre quality relative to the industry standard cultivar (Sicot 74BRF) under both irrigated and dryland field conditions. The selected new line is designated Sicot 714B3F.

Sicot 714B3F is a mid- to full-season maturing variety which has performed well in both irrigated and dryland conditions. Its foliage is dark green. It has a compact growth habit, produces relatively large bolls and has a tendency to fruit earlier in the season, therefore more suited to shorter season than longer season growing areas. Compared to other selected lines, Sicot 714B3F has a longer peduncle length relative to Sicot 746B3F, and a higher number of nodes compared to each of Sicot 748B3F and Sicot 754B3F. Sicot 714B3F is well suited to all growing regions in Australia and offers a high yielding option for short season areas. Sicot 714B3F provided increased yield relative to parental variety Sicot 71BRF in replicated field trials over three years and eight regions (24 sites). The direct comparison showed a 3% increase in yield over Sicot 71BRF, which increase was significant. At higher seed sowing densities, Sicot 71BRF generally had better establishment rates than Sicot 71BRF and several other new lines that were trialled. The plants had a compact growth habit. This variety quickly accumulated fruit (bolls) after flowering.

With regard to fungal disease resistance, Sicot 714B3F had the highest commercially available *Verticillium* disease tolerance ranking (V. Rank of 113(10), Table 5) and was the best variety for growing in fields with heavy levels of *Verticillium* wilt inoculum in the soil. This variety outperformed both Sicot 746B3F and Sicot 748B3F in variety trials in the presence of elevated levels of *Verticillium* wilt. Additionally, the *Fusarium* disease resistance ranking (F. rank) of 130 (7) was a marked improvement over Sicot 71BRF and was considered robust enough for fields with moderate levels of *Fusarium* wilt. The new variety was also highly resistant to bacterial blight caused by *Xanthomonas axonopodis* pv. *malvacearum*.

In dryland production areas it has performed well and achieved an outstanding yield result in a trial using a single skip growth configuration, yielding 11.69 b/ha. Sicot 714B3F has also demonstrated superior establishment in irrigated and dryland conditions over both Sicot 746B3F and Sicot 748B3F. Sicot 714B3F is therefore advantageous in being able to provide a viable plant stand in marginal planting conditions. In full season areas, Sicot 714B3F would be an option for late planting or replant as well in areas where establishment conditions are less than ideal.

Sicot 714B3F is homozygous for each of the transgenes encoding Cry1Ac (transgenic event No. MON531), Cry2Ab (transgenic event MON15985), Vip3A (transgenic event COT102) and the CP4 transgenic event (event MON88913), and has been stably propagated in terms of its phenotype through at least 5 generations.

Thus, according to one aspect of this invention there is provided a plant of the cotton (*Gossypium hirsutum*) variety designated Sicot 714B3F, or a part, cell, tissue or organ thereof, preferably seed. Plants and seed of the cotton variety Sicot 714B3F were generated using a breeding process which began with the parental lines 69801F1 and Sicot 71BRF as a recurrent parent as described herein and as illustrated in the Examples which follow. Once established, Sicot 714B3F can be propagated from seed or alternatively by using tissue culturing techniques, as described herein. In this aspect, the invention also provides seed of the cotton variety designated Sicot 714B3F as well as a cotton plant produced by growing this seed.

Seeds of the cotton variety of this aspect of the present invention can be generated using conventional growing of plants in the field and harvesting by mechanical means, or through breeding and selection techniques which are well known in the art. For example, screening techniques such as molecular marker assisted selection such as, for example, restriction fragment length polymorphism (RFLP), amplified fragment length polymorphism (AFLP), simple sequence polymorphism or microsatellite selection or other genetic marker selection, can be employed in combination with recurrent selection, pedigree breeding, transformation and/or backcrossing to generate the most suitable parental lines used for hybrid seed production.

Cotton is commonly reproduced by self-pollination and fertilization. This type of sexual reproduction facilitates the preservation of plant and variety characteristics during breeding and seed production. The preservation of these characteristics are often important to plant breeders for producing cotton plants having desired traits.

Insect control. Control of insect pests during growing of Sicot 714B3F, its progeny or hybrids produced therefrom is aided by the presence of transgenes encoding the Cry1Ac, Cry2Ab and Vip3A proteins. The genes encoding the Cry proteins, derived from *Bacillus thuringiensis* (Bt) encode proteins that are toxic to Lepidopteran pests of cotton. The Bt proteins, the genes encoding these and the specific transgenic events present in Sicot 714B3F are disclosed in US Patent Applications published as US20040045054 (transgenic event No. 531) and US20040250317 (transgenic event 15985), both hereby incorporated by reference. The Vip3A gene encoding the insecticidal protein derived from *Bacillus* sp. (transgenic event COT102) is disclosed in WO2004/039986, hereby incorporated by reference. The presence of the genes in the plants or plant material may be determined by detection of the genes by PCR or other methods, well known in the art, or by ELISA assays as described in Example 1 below or in the US applications US20040045054 or US20040250317 or the application published as WO2004/039986.

Herbicide tolerance. Sicot 714B3F was also homozygous for a single T-DNA insertion having within it two complete coding regions each encoding a 5-enolpyruvyl shikimate-3-phosphate synthase (EPSPS) protein from *Agrobacterium* sp. strain CP4, derived from the transgenic event MON 88913 (Horak et al, Crop Science 47:268-277, 2007); Cerny et al., Crop Science 50:1375-1384, 2010) that by overexpression of EPSPS provided tolerance to the herbicide glyphosate. This trait was also known as Roundup Ready Flex and allowed for spraying of the plants with glyphosate beyond the 4-leaf stage, providing effective weed control in the cotton crops throughout the growing season.

Disease resistance. As illustrated in the Examples below, Sicot 714B3F also had the important characteristic of having relatively high resistance to *Verticillium* and *Fusarium* wilt diseases. Although its resistance was not complete in that a percentage of plants became infected when grown in a field known to contain *Fusarium*, the degree of resistance as expressed as a *Fusarium* resistance ranking for Sicot 714B3F was 130. The *Fusarium* resistance ranking (F.rank) for a particular line was calculated as the total % for a particular line divided by the total % for the reference variety Sicot 189, expressed as a percentage.

Lint. The invention also provides lint which is obtained from plants of the invention. Sicot 714B3F provided lint that was relatively long and strong for *G. hirsutum*, in combination with high yield and good agronomic performance including a relatively high level of resistance to wilt disease. Lint is preferably harvested by mechanical means from plants grown in the field, and may further be ginned to separate the seed from the fibres. As illustrated in the Examples below, Sicot 714B3F has the important characteristic of producing lint having long fibre length, good strength and mid-range micronaire. When compared to the parental variety Sicot 71BRF, Sicot 714B3F had increased fibre yield and at least the same (and in most trials increased) fibre length and strength. Irrigated trials and seed increase fields growing Sicot 714B3F have consistently produced lint with fibre length scores of at least 37, often at least 38, or even 39 (as 32nds of an inch, so a score of 38 corresponds to 1.20 inches) as well as excellent strength of greater than 30 g/tex, for example about 30.4, and mid-range micronaire of about 4.4. The fibre length of lint obtained from Sicot 714B3F was often at least 1/32nd of an inch longer than lint for Sicot 71BRF under a variety of growth conditions.

The final textile produced from the fibre of Sicot 71BRF also falls within the scope of this invention.

The present invention also provides a method for producing a hybrid cotton seed, which may be an F1 hybrid seed, which comprises crossing a plant of cotton variety Sicot 714B3F with a different cotton plant and harvesting the resultant cotton seed. In this aspect, the invention also extends to hybrid cotton seed produced by this method, a hybrid cotton plant produced by growing such hybrid cotton seed or a part, cell, tissue or organ of such a hybrid cotton plant, and to seed produced by growing this hybrid cotton plant. As described herein, breeding and selection techniques for production of such F1 hybrid cotton plants and seed are well known in the art. The invention extends to a second generation of progeny seed and plants which may be generated by selfing the F1 hybrids to produce F2 seed and plants or by further crossing, and further generations of progeny.

The goal of backcrossing is to alter or substitute one or more defined traits or characteristics in a recurrent parental line. To accomplish this, the defined gene(s) of the recurrent parental line is substituted or supplemented with the desire gene(s) from the non-recurrent line, while retaining essentially all of the rest of the desired genes, and therefore the desired physiological and morphological constitution of the original line. The choice of the particular non-recurrent parent will depend on the purpose of the backcross. One of the major purposes is to add some commercially desirable, agronomically important trait to the plant. The exact backcrossing protocol will depend on the characteristic or trait being altered or added to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred. Depending on the number of backcrosses and the efficacy of the selection of the recurrent parent plant type and genotype, the genetic conformity with Sicot 714B3F of the resulting essentially derived variety may vary between 90% and 100%, preferably between 95% and 100%.

The product of essential derivation is an essentially derived variety, which is, except for example for one, two, three, four or five distinctive characteristics, which characteristics are different as the result of the act of derivation, characterized by the same combination of expression of the characteristics in its phenotype as in the phenotype of the initial variety, which same combination of expression results from the genotype that is nearly identical or almost identical or similar to the genotype of the initial variety. Plants of the essentially derived variety can be used to repeat the process of essential derivation. The result of this process is also a variety essentially derived from said initial variety.

Generally, the nomenclature used herein and the laboratory procedures utilised in the present invention include well known plant breeding and selection techniques. Such techniques are thoroughly explained in the literature. See, for example, Janick, J. (2001) Plant Breeding Reviews, John Wiley & Sons, 252 p.; Jensen, N. F. ed. (1988) Plant Breeding Methodology, John Wiley & Sons, 676 p., Richard, A. J. ed. (1990) Plant Breeding Systems, Unwin Hyman, 529 p.; Walter, F. R. ed. (1987) Plant Breeding, Vol. I Theory and Techniques, MacMillan Pub. Co.; Slavko, B. ed. (1990) Principles and Methods of Plant Breeding, Elsevier, 386 p.; and Allard, R. W. ed. (1999) Principles of Plant Breeding, John-Wiley & Sons, 240 p. The ICAC Recorder. Vol. XV no. 2: 3-14; and Davis D. D. (1978) Hybrid Cotton: Specific Problems and Potentials. Adv. Agron. 30: 129-1571; all of which are incorporated by reference as if fully set forth herein. Other general references are provided throughout this document. The procedures therein are believed to be well known in the art and are provided for the convenience of the reader. All the information contained therein is incorporated herein by reference.

In another aspect, the present invention provides a tissue culture of regenerable cells of the cotton variety Sicot 714B3F, as well as a cotton plant regenerated from the tissue culture. As used herein the phrase "tissue culture" refers to plant cells or plant parts maintained in vitro from which cotton plants can be generated, including plant protoplasts, plant calli and plant tissue clumps. Furthermore, the present invention provides plant cells that are intact in plants, or parts of plants, such as seeds, leaves, stems, cotyledons, hypocotyls, pollen cells, roots, root tips, anthers, ovules and embryos, from which tissue cultures can be established.

Techniques of generating plant tissue culture and regenerating plants from tissue culture are well known in the art. For example, such techniques are set forth by Vasil (1984), Cell Culture and Somatic Cell Genetics of Plants, Vol I, II, III Laboratory Procedures and Their Applications, Academic Press, New York; Green et al. (1987), Plant Tissue and Cell Culture, Academic Press, New York; Weissbach and Weissbach (1989), Methods for Plant Molecular Biology, Academic Press; Gelvin et al. (1990), Plant Molecular Biology Manual, Kluwer Academic Publishers; Evans et al. (1983) Handbook of Plant Cell Culture, MacMillian Publishing Company, New York. A tissue culture can be generated from cells or protoplasts of a tissue selected from the group consisting of seeds, leaves, stems, pollen, anthers, ovules, embryos, preferably cotyledons or hypocotyls. Techniques of generating cotton plant tissue culture and regenerating cotton plants from tissue culture are described, for example, by Umbeck et al. (1987), Bio/Technology 5:263-266; Firoozabady et al. (1987), Plant Mol. Biol. 10:105-116; Finer J. (1988), Plant Cell Rep. 6:231-234 and U.S. Pat. Nos. 5,986,181; 5,846,797.

In yet another aspect, the present invention provides a method of producing a cotton plant is transgenic for additional transgenes, which method comprises transforming a plant of the cotton variety Sicot 714B3F, or a part, cell, tissue or organ thereof, with a nucleic acid molecule comprising a foreign or non-endogenous nucleotide sequence, or an additional or modified endogenous nucleotide sequence, to provide additional transgenes other than those in Sicot 714B3F. The nucleic acid molecule comprising such an additional transgene is preferably a gene construct which comprises a coding sequence and one or more expression control sequences. Preferred transgenes are those encoding a gene or genes for modifying oil quality such as those described in WO2010/009499, or for reducing gossypol in the seed as described in U.S. Pat. No. 7,999,148, both hereby incorporated by reference.

In this aspect, the present invention also includes a cotton plant produced by the method described above or a part, cell, tissue or organ thereof. The invention also includes a seed of the cotton plant comprising the additional transgene as well as a progeny plant produced by growing this seed, or a part, cell, tissue or organ of such a progeny plant, comprising the additional transgene.

Transgenes can be introduced into the plant using any of a variety of established transformation methods well-known to person skilled in the art, such as: Klee, H., et al. (1989) Plant Gene Vectors and Genetic Transformation: Plant Transformation Systems Based on the use of *Agrobacterium tumefaciens*, Cell Culture and Somatic Cell Genetics of Plants; and Koncz, C., et al (1986) Molecular and General Genetics. Techniques for transforming cotton plants are described in Umbeck et al. (1987) Bio/Technology 5:263-266; Firoozabady et al. (1987) Plant Mol. Biol. 10:105-116; Finer and McMullen (1990) Plant Cell Rep. 8:586-589]

Bayley et al. (1992) Theo. Appl. Genet. 83:45-649; Perlak et al. (1990), Bio/Technology 8:939-943; and U.S. Pat. Nos. 5,986,181; 5,846,797.

Additional transgenes may also be introduced into Sicot 714B3F plants by crossing these plants with a suitable cotton variety which contains a desired transgene, optionally followed by one or more backcrosses to Sicot 714B3F with selection of the desired combination of characteristics.

Availability of Sicot 714B3F

Sicot 714B3F seed is available commercially from Cotton Seed Distributors, Wee Waa, New South Wales, Australia. A deposit of seed of the cotton variety Sicot 714B3F is also maintained at the CSIRO seed store, Australian Cotton Research Institute, Narrabri, New South Wales, Australia, and access to deposited seed will be available during the pendency of this application. Seed of the cotton variety Sicot 714B3F has also been deposited in accordance with the Budapest Treaty requirements in the American Type Culture Collection, 10801 University Boulevard, Manassas, Va. 20110, United States of America, under ATCC Accession No. PTA-126051.

Reference is now made to the following Examples which further illustrate the present invention in a non-limiting way.

EXAMPLES

Example 1

Materials and Methods

ELISA Assay to Detect Cry1Ac or Cry2Ab Gene Expression.

Expression of the Cry2Ab protein in cotton plants was detected by ELISA assays using an antibody raised against Cry2Aa but which also reacts with Cry2Ab protein, as follows. The ELISA assay for Cry1Ac protein was performed in an analogous manner using an antibody raised against Cry1Ab which also reacts with Cry1Ac protein.

ELISA coating buffer contained, per litre, sodium carbonate ($Na_2CO_3$), 1.59 g; sodium hydrogen carbonate ($NaHCO_3$), 2.93 g and sodium chloride (NaCl), 8.77 g made up to 1000 ml with distilled water. 10× PBST contained per 5000 ml: NaCl, 400 g; sodium hydrogen phosphate ($Na_2HPO_4.12H_2O$), 145 g; potassium dihydrogen phosphate ($KH_2PO_4$), 10 g; potassium chloride (KCl), 10 g; 35 ml of Tween 20; made up to 5000 ml with distilled water. 1× PBST was a 1/10 dilution with distilled water. ELISA substrate buffer contained, per litre, diethanolamine, 97 ml; distilled water, 800 ml; sodium azide, 0.2 g. The pH was adjusted to 9.8 with concentrated hydrochloric acid (HCl), the volume made up to 1000 ml with distilled water and stored at 4° C. in the dark in an airtight container. ELISA extraction buffer contained per litre: NaCl, 8 g; $KH_2PO_4$, 3 g; $Na_2HPO_4 12H_2O$, 29 g; KCl, 2 g; sodium azide, 0.2 g; PVP-40, 20 g; Tween 20 (SG 1.10), 0.5 ml; made up to 1000 ml with distilled water. The solution was adjusted to pH 7.4.

On day one of the ELISA procedure, ELISA plates (Maxisorp, Nunc, Rochester N.Y. or similar) were coated with an ammonium sulphate precipitated Cry2A specific rabbit IgG fraction (at 1 µg/ml) in ELISA coating buffer (200 µl per well) and allowed to bind overnight at 4° C. The next day, the plates were washed twice with PBST, rotating the plates after the first wash so as to get a thorough washing. These plates were used immediately or stored in snap-lock bags at −20° C. Seeds were sectioned on day one, clipping one end of the seed (approximately ⅓ seed) using dog nail clippers and keeping the pointy end. The seeds were imbibed on very wet cottonwool using distilled water at room temperature overnight. On day two, the embryo was squeezed out of the seed into 96 well racked collection tubes (ThermoTrace) each containing a 3 mm chrome steel ball bearing, one embryo per tube. To each tube, 400 µl of Extraction Buffer was added, the tubes capped firmly and mixed in a Mixer Mill (Qiagen) at 30 shakes/per second for 2 minutes to disrupt the tissues. The racks of tubes were rotated and shaken a further 2 minutes. Sediment was allowed to settle for five minutes and then the caps removed. Coated ELISA plates were prepared by adding 180 µl of 1× PBST+0.2% chicken ovalbumin and Cry2A specific rabbit IgG conjugated to alkaline phosphatase using glutaraldehyde at 1/2000 dilution per well. 20 ∞l of ground seed sample was added per well using wide bore tips (ThermoTrace). The plates were covered and left overnight at 4° C. in a moist, sealed box to prevent drying out of the samples. On day three, samples were decanted and the wells washed twice with PBST, rotating the plates each wash to ensure thorough washing. 150 µl of Substrate Buffer containing Sigma 104 Phosphatase Substrate (nitrophenylphosphate) (56 mg/100 ml) was added to each well. Plates were left at room temperature for 1 to 2 hours for colour to develop. Positive samples (ie seed extracts containing Cry2A protein) gave a bright yellow colour. Negative samples stayed clear. The colour reaction could be stopped by adding 30 µl 0.3 M sodium hydroxide per well.

Plant Characteristics

The leaf hair phenotype of plants was assessed visually and given a score from 0 (glabrous) to 4 (hairy). Scores of <4 were preferred. Resistance was assessed to the disease bacterial blight of cotton, caused by *Xanthomonas axonopodis* pv. *malvacearum*. Plants were selected that were free of water soaked lesions two weeks or more after a spray with a suspension of *X. axonopodis* cells, race 18.

Resistance was also assessed to *Fusarium* and *Verticillium* wilts, caused by the fungi *Fusarium oxysporum* f. sp. *vasinfectum* and *Verticillium dahliae*, respectively, by growing the plants in the soil known to contain the organisms. The *Fusarium* fungus affected susceptible cotton seedlings and often more mature plants. Affected plants were first darker green and stunted, followed by yellowing of the leaves and dying or loss of foliage. Symptoms typically first appeared on lower leaves around the time of first flower. The leaf margins then wilted, turning yellow and then brown. Infected plants fruited earlier than normal with smaller bolls that opened prematurely. A diagonal cut across the stem typically revealed vascular discoloration just beneath the bark extending down the tap root. Wilting occurred rapidly following rain preceded by a dry spell. *Verticillium* wilt fungus was also known to infect the roots and grow in the xylem, blocking water uptake and thereby causing wilt symptoms. Affected seedlings typically yellowed, dried out and died. Larger plants were stunted and leaves showed a yellowing of the margin and the areas between the main veins. These areas eventually died leaving leaves with a scorched appearance. Symptoms typically first appear on the lower leaves. A dark-brown discolouration of the water-conducting tissues of the roots and stem was also evident in susceptible plants. Severely affected plants tended to shed leaves and bolls. Resistance to *Fusarium* and *Verticillium* was scored relative to known resistant cultivars, in particular Sicot 189.

Fibre Quality and Yield

Yield (Yld) of lint was expressed as kg/ha. Lint (seed-free) was obtained from harvested (seed) cotton by ginning on a 20 saw gin and weighed. Lint % (gin turnout) was expressed as the weight of the ginned lint as a percentage of the weight of the input seed cotton. Values between 40 and 44 were preferred. Fibre quality was measured on duplicate samples using an Uster HVI900SA. Measurements were made of fibre length (len), fibre strength (str), uniformity (uni), short fibre index (sfi), elongation (el), micronaire (mic), maturity (mr), maturity percentage (mp), fineness (fin) and neps per gram. Long and strong fibres with intermediate micronaire (3.8 to 4.5) were preferred.

Example 2

Plants of *G. hirsutum* cv. Sicot 71BRF (Australian Plant Breeders Rights Application No. 2007/285) were crossed with pollen from a proprietary breeding line 69801F1 in a PC2 glasshouse at the Australian Cotton Research Institute (ACRI), Narrabri, New South Wales, Australia. From these crosses, F1 progeny were selected on the basis of Cry1Ac, Cry2Ab and Vip3A expression, plant habit and morphology including smooth leaf. Following a selfing generation in the greenhouse, 502 plants were selected that comprised all three transgenes plus the glyphosate tolerance gene. Following progeny row testing for yield, disease resistance and fibre quality, 70 lines were progressed to replicated, multi-site trials. Emphasis was placed on lint yield, fibre quality (length and strength) and resistance to *Verticillium* and *Fusarium* wilt diseases. The data for the best 16 lines derived from the 502 plants is shown in Table 1. Line 404 corresponds to Sicot 714B3F.

Example 3

Field Trial Results

The selected line was grown at ten trial sites in the 2014/15 season and compared to other selected lines and control varieties. The cultivar Sicot 74BRF was grown as a comparator in the remainder of each field. In direct comparisons with Sicot 74BRF at six trial sites, Sicot 714B3F showed an improvement in average emergence of seedlings and establishment. Sicot 714B3F achieved approximately 10% better establishment relative to Sicot 74BRF (Table 2, data from six trial sites), indeed it was the best of the new selected lines. Table 3 shows the lint yield and quality from six of these trials that included all four selected lines within the trial and therefore conformed to industry standards.

TABLE 2

Establishment of selected cotton lines after sowing (2014/15 trials)

| Selected line or cultivar | Average Establishment (%) | Range |
| --- | --- | --- |
| Sicot 746B3F & Sicot 748B3F | 67.5 | 46-87 |
| Sicot 754B3F | 67.8 | 49-80 |
| Sicot 714B3F | 71.2 | 58-87 |
| Sicot 74BRF (control) | 60.0 | 28-8 |

TABLE 1

Mean parameters for the 16 best lines grown across four field sites derived from 502 plants in 2012/13 season compared to Sicot 71BRF.

| Line ID | Plant Height | LP | MEAN | LEN | UNI | SFI | STR | EL | MIC | PM | FIN | Fov SURV |
| --- | --- | --- | --- | --- | --- | --- | --- | --- | --- | --- | --- | --- |
| 69804-63 | 3.8 | 42.0 | 2656 | 1.22 | 83.8 | 9.2 | 29.9 | 6.7 | 4.3 | 74.2 | 176 | 34 |
| 69804-67 | 3.9 | 42.5 | 2711 | 1.25 | 83.3 | 8.8 | 29.8 | 6.3 | 4.1 | 73.7 | 161 | 40 |
| 69804-74 | 3.9 | 42.1 | 2680 | 1.21 | 83.1 | 9.9 | 29.0 | 6.6 | 4.3 | 76.3 | 164 | 43 |
| 69804-168 | 3.2 | 42.5 | 2692 | 1.22 | 83.6 | 9.0 | 29.6 | 7.5 | 4.3 | 76.1 | 172 | 40 |
| 69804-170 | 3.9 | 43.3 | 2814 | 1.23 | 82.5 | 9.9 | 29.2 | 6.2 | 4.0 | 75.2 | 154 | 33 |
| 69804-216 | 3.4 | 41.7 | 2756 | 1.21 | 83.0 | 9.7 | 29.0 | 6.7 | 4.1 | 76.5 | 164 | 31 |
| 69804-323 | 4.0 | 41.3 | 2685 | 1.21 | 82.9 | 10.1 | 29.3 | 6.7 | 4.2 | 77.2 | 167 | 42 |
| 69804-345 | 4.4 | 42.9 | 2664 | 1.24 | 83.9 | 8.6 | 30.4 | 6.2 | 4.2 | 75.1 | 171 | 43 |
| 69804-404 | 3.9 | 42.9 | 2752 | 1.20 | 83.8 | 9.0 | 30.4 | 6.6 | 4.4 | 77.8 | 180 | 30 |
| 69804-450 | 3.5 | 42.8 | 2724 | 1.22 | 83.0 | 9.6 | 29.1 | 6.6 | 4.2 | 76.3 | 169 | 37 |
| 69804-452 | 3.5 | 43.7 | 2830 | 1.20 | 83.1 | 9.8 | 29.7 | 6.6 | 4.2 | 76.7 | 167 | 20 |
| 69804-463 | 3.5 | 42.4 | 2812 | 1.21 | 83.4 | 9.6 | 30.0 | 6.6 | 4.3 | 75.6 | 171 | 34 |
| 69804-490 | 3.9 | 41.6 | 2638 | 1.20 | 83.4 | 9.4 | 30.0 | 6.5 | 4.3 | 77.1 | 169 | 45 |
| 69804-506 | 4.0 | 42.0 | 2700 | 1.24 | 82.7 | 9.7 | 28.9 | 6.0 | 4.1 | 73.1 | 169 | 38 |
| 69804-516 | 3.8 | 42.0 | 2697 | 1.23 | 83.9 | 8.8 | 30.4 | 6.4 | 4.4 | 77.7 | 172 | 32 |
| 69804-572 | 3.6 | 42.7 | 2707 | 1.24 | 83.1 | 9.4 | 30.0 | 6.4 | 4.2 | 76.8 | 168 | 34 |
| Sicot 71BRF | 3.7 | 42.0 | 2653 | 1.20 | 83.0 | 10.0 | 28.7 | 6.6 | 4.3 | 77.1 | 168 | 34 |

Plant Height = rating from 1 (short) to 5 (tall);
LP = proportion of lint in seed cotton sample (gin turnout);
MEAN = mean lint yield in kg/ha across four field sites;
LEN = 2.5% span length as measured by HVI (inches);
UNI = uniformity index;
SFI = short fibre index;
STR = strength (g/tex);
EL = elongation (%);
MIC = micronaire;
PM = % maturity of fibre as measured by FMT3;
FIN = fineness (millitex) as measured by FMT3;
Fov SURV = % survival in *Fusarium* nursery

TABLE 3

Lint yield and some quality parameters for selected lines (2014/15 trials)

| Selected line or cultivar | Lint Yield | Relative Yield (%) | Fibre length (Len) | Micronaire (Mic) |
|---|---|---|---|---|
| Sicot 746B3F & 748B3F | 14.1 | 102.3% | 1.20 | 4.2 |
| Sicot 754B3F | 13.0 | 94.5% | 1.25 | 4.0 |
| Sicot 714B3F | 13.6 | 98.8% | 1.19 | 4.0 |
| Sicot 74BRF (control) | 13.8 | 100% | 1.19 | 4.2 |

Further trials were carried out measuring yield, quality and disease ratings on selected lines containing the two Cry genes and Vip3A over three to four seasons across a number of regional sites. Table 4 summarizes this longer term data, and Table 5 provides disease rankings for the selected lines.

TABLE 4

Small plot trial data for selected lines (3 seasons, 18 sites)

| Trial Variety | Yield (bales/ha) | Rel. Yield % | Gin turn out % | Length | Strength | Mic |
|---|---|---|---|---|---|---|
| Sicot 714B3F | 14.0 | 96 | 42.2 | 1.20 | 30.4 | 4.5 |
| Sicot 748B3F | 14.6 | 101 | 44.0 | 1.24 | 31.0 | 4.6 |
| Sicot 746B3F | 14.6 | 101 | 45.3 | 1.21 | 30.8 | 4.6 |
| Sicot 754B3F | 13.9 | 96 | 43.1 | 1.25 | 31.4 | 4.5 |
| Sicot 71BRF | 13.6 | 94 | 41.0 | 1.22 | 30.2 | 4.4 |
| Sicot 74BRF | 14.5 | 100 | 44.3 | 1.23 | 30.5 | 4.7 |
| Sicot 75BRF | 14.0 | 97 | 43.2 | 1.26 | 30.9 | 4.6 |

TABLE 5

Disease rankings for selected lines

| Variety | F. rank (*Fusarium* resistance) | V. rank (*Verticillium* resistance) |
|---|---|---|
| Sicot 746B3F | 139(5) | 101(10) |
| Sicot 748B3F | 135(5) | 101(10) |
| Sicot 754B3F | 155(5) | 91(10) |
| Sicot 714B3F | 130(7) | 113(10) |

Further Evaluation

An extensive trial and evaluation program was carried out in the 2015/16 season to fully test, monitor and evaluate the new selected lines. Commercial scale fields spanning the length and breadth of the Australian cotton growing areas were used including 48 irrigated sites and 14 dryland sites. Additional monitoring and evaluation was also carried out in 58 irrigated and 10 dryland cotton fields in collaboration with commercial cotton growers.

TABLE 6

Yield and fibre comparison of two selected lines (3 irrigated trials, one season)

| Parameter | Sicot 707B3F | Sicot 714B3F |
|---|---|---|
| Yield (bales/ha) | 12.74 | 13.16 |
| Yield (bales/acre) | 5.16 | 5.33 |
| Staple (dec) | 1.16 | 1.16 |
| Micronaire | 4.5 | 4.4 |
| Strength (g/tex) | 31.0 | 31.0 |
| Gin turnout | 42.2 | 41.5 |
| Uniformity | 82.8 | 82.7 |

TABLE 7

Yield and fibre comparison of two selected lines (13 dryland trials, one season)

| Parameter | Sicot 714B3F | Sicot 748B3F |
|---|---|---|
| Yield (bales/ha) | 4.59 | 4.59 |
| Yield (bales/acre) | 1.86 | 1.86 |
| Staple (dec) | 1.11 | 1.13 |
| Micronaire | 3.7 | 4.1 |
| Strength (g/tex) | 28.4 | 28.9 |
| Gin turnout | 40.1 | 42.8 |
| Uniformity | 80.4 | 80.3 |

TABLE 8

Yield and fibre comparison of two selected lines (43 irrigated trials, one season)

| Parameter | Sicot 714B3F | Sicot 746B3F |
|---|---|---|
| Yield (bales/ha) | 12.47 | 13.03 |
| Yield (bales/acre) | 5.05 | 5.27 |
| Staple (dec) | 1.17 | 1.18 |
| Micronaire | 4.4 | 4.4 |
| Strength (g/tex) | 30.1 | 30.7 |
| Gin turnout | 40.9 | 44.3 |
| Uniformity | 82.1 | 81.6 |

Example 4

Production of Hybrid Seed from Sicot 714B3F

Plants of Sicot 714B3F are crossed with cotton plants of a variety that is transgenic for a gene conferring modified fatty acid composition in the seedoil (WO201/009499). The F1 progeny plants are backcrossed to Sicot 714B3F as a recurrent parent for several generations to provide Sicot 714B3F with increased oleic acid and reduced palmitic acid in the total fatty acid content of the seedoil, providing a healthier cotton seedoil. Plants of Sicot 714B3F are also crossed in a similar fashion with cotton plants having other desirable features such as additional disease resistance genes or reduced gossypol content in the seed.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Unless the context indicates otherwise, the reference to any prior art in this specification is not, and should not be, taken as an acknowledgment or any form of suggestion that the prior art forms part of the common general knowledge in Australia.

The invention claimed is:

1. A plant of the cotton variety Sicot 714B3F, or a plant part, comprising a cell, tissue or organ thereof, wherein the plant or plant part comprises the genotype of Sicot 714B3F, and wherein representative seed of variety Sicot 714B3F have been deposited under ATCC Accession Number PTA-126051.

2. Seed of the cotton variety Sicot 714B3F, the seed comprising the genotype of Sicot 714B3F, wherein representative seed of variety Sicot 714B3F have been deposited under ATCC Accession Number PTA-126051.

3. A cotton plant produced by growing the seed of claim 2, or a plant part, comprising a cell, tissue or organ of said plant, wherein the cotton plant or plant part, comprises the genotype of Sicot 714B3F.

4. A tissue culture of regenerable cells of the cotton plant of claim 1, the cells comprising the genotype of Sicot 714B3F.

5. A tissue culture of regenerable cells generated from a part, tissue, or organ of the cotton plant of claim 1, the cells comprising the genotype of Sicot 714B3F, wherein the tissue culture regenerates plants capable of expressing all the morphological and physiological characteristics of cotton variety Sicot 714B3F.

6. The tissue culture of claim 5, wherein said tissue culture is generated from cells or protoplasts of a tissue selected from the group consisting of seeds, leaves, stems, pollen, anthers, ovules, embryos, cotyledon and hypocotyl.

7. A cotton plant regenerated from the tissue culture of claim 4, or a part, cell, tissue or organ of said regenerated cotton plant, wherein said regenerated cotton plant has all the morphological and physiological characteristics of Sicot 714B3F.

8. A method for producing F1 hybrid cotton seed, comprising crossing the cotton plant of claim 1 with a different cotton plant, and harvesting the resultant F1 hybrid cotton seed.

9. The method of claim 8, further comprising obtaining a cotton plant from the F1 hybrid cotton seed, and optionally obtaining progeny plants or seed of a second or subsequent generation.

10. The F1 hybrid cotton seed produced by the method of claim 8.

11. A hybrid cotton plant produced by growing the F1 hybrid cotton seed of claim 10, or a part, cell, tissue or organ of said hybrid cotton plant.

12. A method of producing cotton seed, comprising growing the hybrid cotton plant of claim 11 and harvesting the resultant seed.

13. A method of producing a transgenic cotton plant, comprising transforming the cotton plant of claim 1, or a cell, tissue or organ thereof, with a nucleic acid molecule comprising a non-endogenous nucleotide sequence, a modified endogenous nucleotide sequence, and/or an additional copy of an endogenous nucleotide sequence.

14. The method of claim 13, wherein said nucleic acid molecule also comprises one or more expression control sequences.

15. A cotton plant produced by the method of claim 13, the cotton plant comprising the genotype of Sicot 714B3F with said nucleic acid molecule, and otherwise expressing all the morphological and physiological characteristics of Sicot 714B3F, or a plant part comprising a cell, tissue, or organ thereof, the plant part comprising the genotype of Sicot 714B3F with said nucleic acid molecule.

16. Seed of the transgenic cotton plant of claim 15, the seed comprising the genotype of Sicot 714B3F with said nucleic acid molecule.

17. A plant produced by growing the seed of claim 16, or a cell, tissue or organ of said plant, the plant, cell, tissue or organ comprising the genotype of Sicot 714B3F with said nucleic acid molecule and otherwise expressing all the morphological and physiological characteristics of Sicot 714B3F.

18. A method of producing lint, comprising the steps of growing the cotton plant of claim 1 and harvesting lint from said cotton plant.

19. The method of claim 18, further comprising the step of ginning the lint so as to separate the lint from seed.

* * * * *